United States Patent [19]
Winter

[11] Patent Number: 4,826,487
[45] Date of Patent: May 2, 1989

[54] ALIGNMENT BUTTON FOR STEREOTAXIC PLUG AND METHOD OF USING THE SAME
[75] Inventor: Arthur Winter, Short Hills, N.J.
[73] Assignee: Victory Engineering Company, Springfield, N.J.
[21] Appl. No.: 46,244
[22] Filed: May 4, 1987
[51] Int. Cl.⁴ ............................................. A61B 19/00
[52] U.S. Cl. .................. 604/175; 128/303 B
[58] Field of Search ...................... 128/303 B; 604/175
[56] References Cited
U.S. PATENT DOCUMENTS
4,629,451 12/1986 Winters et al. ...................... 604/175

Primary Examiner—Michael H. Thaler
Attorney, Agent, or Firm—Thomas R. Morrison

[57] ABSTRACT

An alignment button includes cannula and radiopaque markers exactly mimicing corresponding elements in a stereotaxic array plug. The stereotaxic array plug is installed in an opening in the skull and the scalp is closed over it. The alignment button is sutured in place with its cannula exactly aligned with corresponding cannula in the stereotaxic array plug. Alignment is performed using medical imaging capable of showing simultaneously the radiopaque marker in both elements. In one embodiment of the invention, jaws protrude inward into the cannula to stabilize a medical device inserted therethrough. In a further embodiment of the invention, the alignment button is affixed over soft tissue without being accompanied by a stereotaxic array plug.

7 Claims, 4 Drawing Sheets

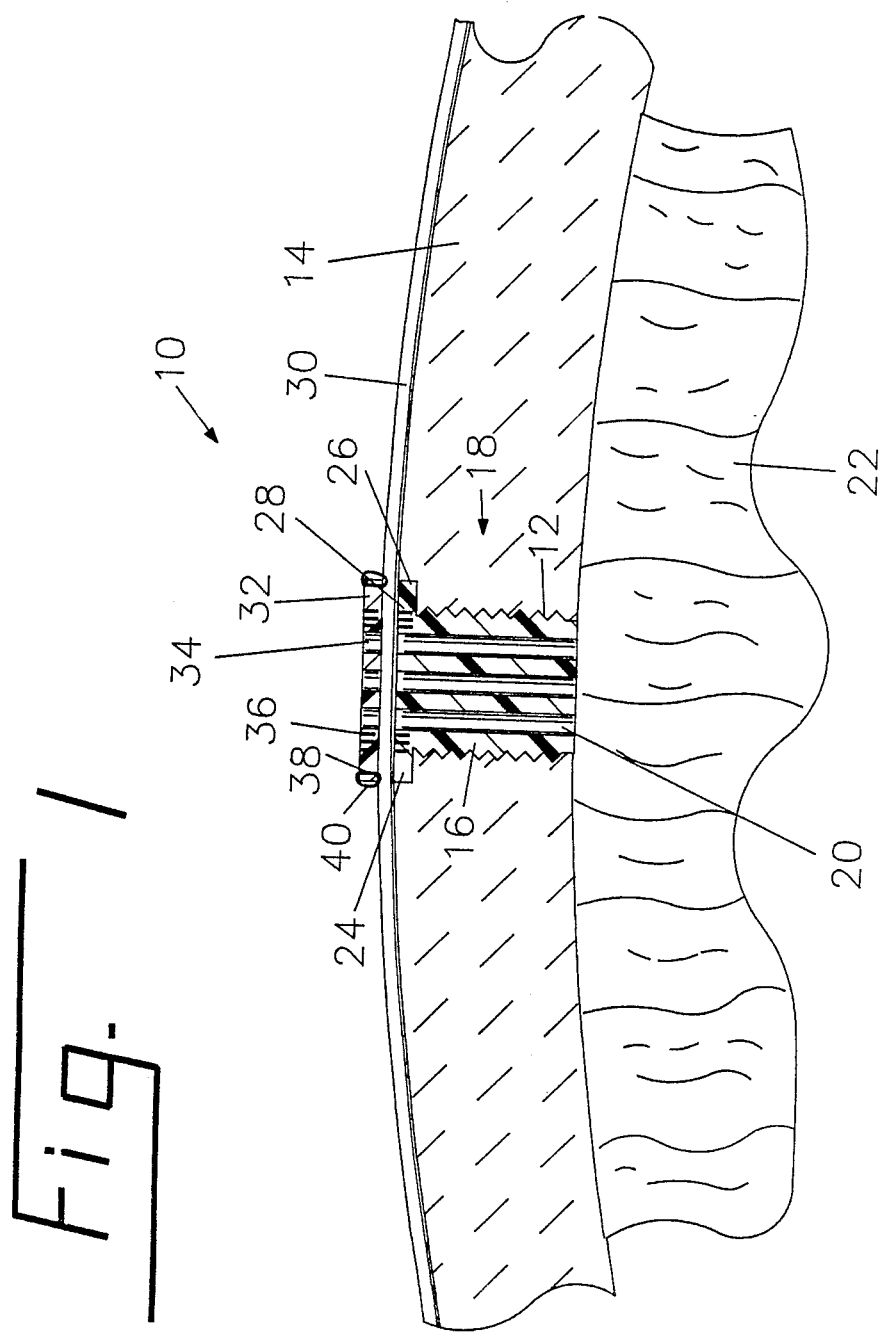

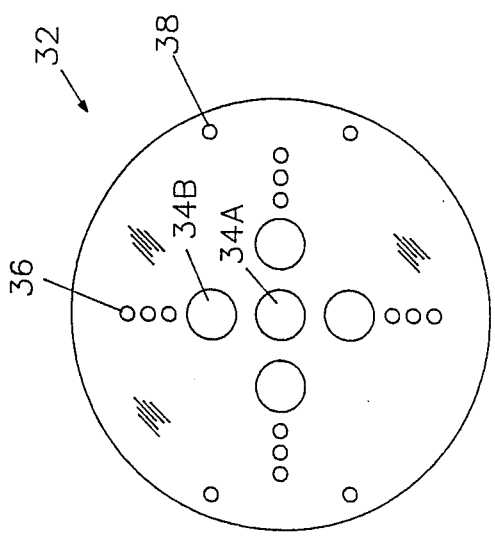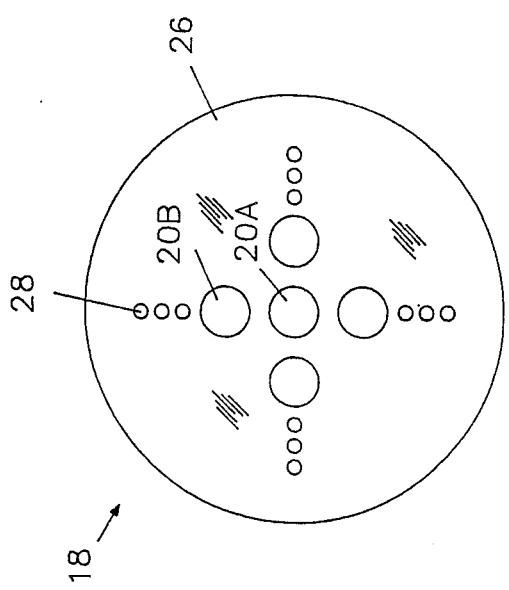

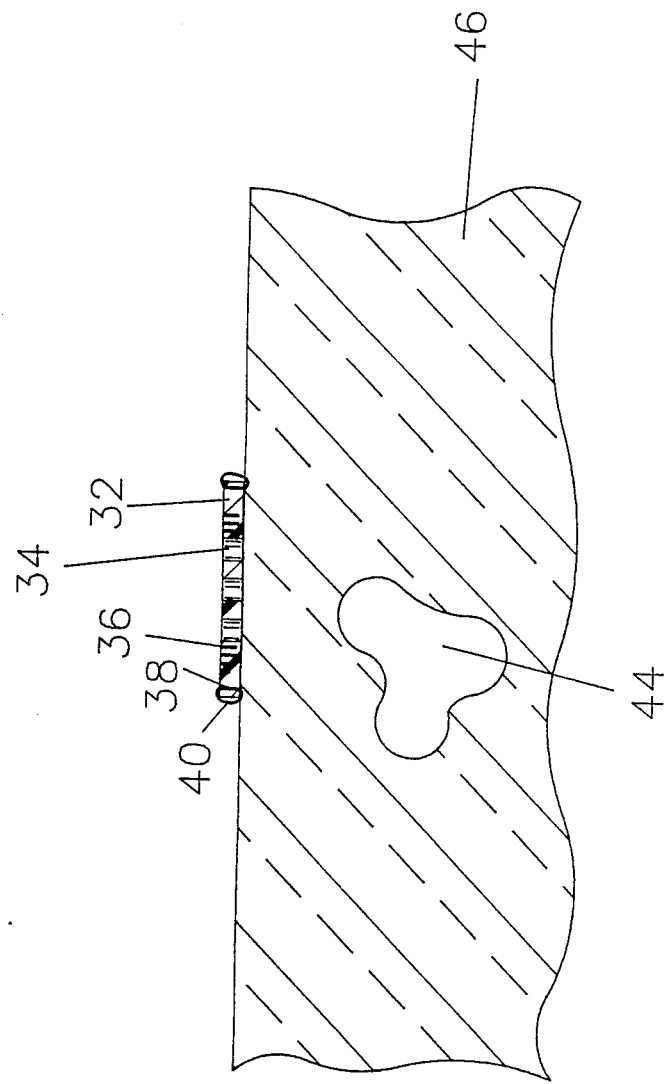

ALIGNMENT BUTTON FOR STEREOTAXIC PLUG AND METHOD OF USING THE SAME

BACKGROUND OF THE INVENTION

The present invention relates to medical treatment and, more particularly, to devices for aligning devices for intrusive entry into a portion of a body requiring medical treatment.

In my prior U.S. Pat. No. 4,629,451 I disclosed a stereotaxic array plug for insertion into the skull of a patient. The plug included a plurality of cannula, or holes, therethrough capable of guiding the insertion of a catheter, and the like, into a predetermined location within the brain of a patient. The devices which may be guided into the brain includes a multi-lumen catheter containing a microwave antenna and a thermistor for hyperthermic treatment of brain tumors. The latter device is disclosed in my allowed U.S patent application Ser. No. 779.285 now matured into U.S, Pat. No. 4,681,122. The disclosures of both of the above references are incorporated herein by reference.

Treatment for brain tumors may continue for times measured in days or months. The danger of infection requires that the opening in the scalp required for drilling and tapping the hole through the skull for insertion of the stereotaxic array plug must be closed immediately and must remain closed until the plug is removed at the end of treatment. It thus becomes a problem, with the scalp closed over the stereotaxic array plug, to find the hole for insertion of catheters and other medical devices through the scalp.

As a partial solution, my referenced stereotaxic array plug employs radiopaque markers in a predetermined pattern on the plug. The radiopaque markers are disposed in a fixed relation to the cannula. Accordingly, the radiopaque markers visible on an X-ray, CAT, NMR or SPECT image may be used to guide the physician in locating the desired cannula. This technique carries the disadvantage that it must be repeated each time treatment is to be performed.

In addition to treatment of tumors in the brain, means are required for guiding treatment to tumors in soft tissue such as, for example, the breast.

OBJECTS AND SUMMARY OF THE INVENTION

Accordingly, it is an object of the invention to provide a technique for locating cannula in a stereotaxic array plug which overcomes the drawbacks of the prior art.

It is a further object of the invention to provide a locating button having cannula and radiopaque markers exactly imaging corresponding cannula and radiopaque markers on a stereotaxic array plug installed in a skull. The cannula in the locating button are positioned in exact alignment with corresponding cannula in the stereotaxic array plug. The button is then sutured in place. Alignment is performed using the images of the two sets of radiopaque markers simultaneously visible on an X-ray or nuclear magnetic resonance image.

It is a still further object of the invention to provide a locating button containing a plurality of cannula and a pattern of radiopaque markers having a predetermined positional relationship to the plurality of cannula. The locating button further includes means for permitting it to be sutured in place over a location requiring treatment by insertion of a medical device through at least one of the cannula.

Briefly stated, the present invention provides an alignment button having cannula and radiopaque markers exactly mimicing corresponding elements in a stereotaxic array plug. The stereotaxic array plug is installed in an opening in the skull and the scalp is closed over it. The alignment button is sutured in place with its cannula exactly aligned with corresponding cannula in the stereotaxic array plug. Alignment is performed using medical imaging capable of showing simultaneously the radiopaque marker in both elements. In one embodiment of the invention, jaws protrude inward into the cannula to stabilize a medical device inserted therethrough. In a further embodiment of the invention, the alignment button is affixed over soft tissue without being accompanied by a stereotaxic array plug.

According to an embodiment of the invention, there is provided a stereotaxic array locating system for locating a displacement and angle of insertion of a medical instrument, comprising: a stereotaxic array plug, the stereotaxic array plug including a first plurality of first cannula disposed in a first pattern, the stereotaxic array plug further including a second plurality of first markers in a second pattern, the second pattern having a predetermined relationship to the first pattern, the first markers being of a type visible on a medical imaging device, the stereotaxic array plug including means for permitting insertion thereof into an opening in a skull, a marker button, the marker button including a third plurality of second cannula disposed in a third pattern, the marker button further including a fourth plurality of second markers in a fourth pattern, the second markers being of a type visible on the medical imaging device, the marker button further including means for permitting stable attachment thereof to a scalp, the third pattern being identical to the first pattern, the second pattern being identical to the fourth pattern, and the first markers and the second markers being capable of simultaneous imaging by the medical imaging device, whereby congruence between the first and second markers resulting in congruence between the first and second cannula is attainable.

According to a feature of the invention, there is provided a method for installing a stereotaxic array locating system comprising: installing a stereotaxic array plug in an opening in a skull, the stereotaxic array plug being of a type including a first plurality of first cannula disposed in a first pattern and a second plurality of first markers in a second pattern, the second pattern having a predetermined relationship to the first pattern, closing a scalp over the stereotaxic array plug, suturing a marker button over the scalp, the marker button being of a type including a third plurality of second cannula disposed in a third pattern and a fourth plurality of second markers in a fourth pattern, the first and third patterns being identical and the second and fourth patterns being identical, the second markers being of a type visible on the medical imaging device, and the step of suturing including aligning the second and fourth patterns using the medical imaging device simultaneously imaging the second and fourth patterns, whereby the first and third patterns are congruent.

According to a further feature of the invention, there is provided a marker button comprising: a disk, a first plurality of cannula in a first predetermined pattern through the disk, a second plurality of markers in a second predetermined pattern on the disk, the markers including means for rendering them visible on a medical imaging device, the second predetermined pattern having a predetermined relationship to the first predetermined pattern, and means for stably affixing the disk to flesh.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a cross section through a portion of a skull showing a stereotaxic array plug installed therein with an aligned locating button.

FIG. 2 is a top view of the stereotaxic array plug of FIG. 1.

FIG. 3 is a top view of the locating button of FIG. 1.

FIG. 6 is a cross section showing a locating button used for treatment of a tumor in soft tissue.

DETAILED DESCRIPTION OF THE PREFERRED EMBODIMENT

Figure 4:
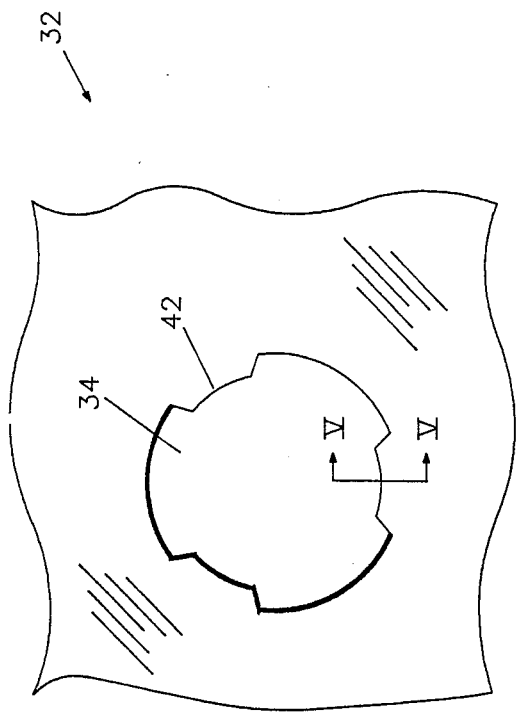
FIG. 4 is a close-up view of one of the cannula of FIG. 3 showing jaws therein.

Referring to FIG. 1, there is shown, generally at 10, a stereotaxic locating system according to an embodiment of the invention. A threaded opening 12 in a pericranium 14 receives a threaded body 16 of a stereotaxic plug 18. A plurality of cannula 20 pass through threaded body 16 to permit insertion of medical devices in a brain tissue 22 lying therebelow. An upper end of stereotaxic plug 18 preferably includes a flange 24 which is preferably fitted into a counterbore 26 in pericranium 14.

A plurality of marker bores 28 are disposed on flange 24 in a predetermined pattern with respect to cannula 20. Each marker bore 28 is filled with a radiopaque marking material such as, for example, gold. The pattern formed by marker bores 28, visible on an X-ray or nuclear magnetic resonance image is useful for determining the position of stereotaxic plug 18 with respect to treatment sites in brain tissue 22 and the positions of cannula 20.

After insertion, stereotaxic plug 18 is covered by a scalp 30 in order to reduce the danger of infection.

A marker button 32 contains marker cannula 34 and radiopaque markers 36 in a precise image of those in stereotaxic plug 18. A plurality of suture holes 38 about the edge of marker button 32 permit fixing it in place using, for example, sutures 40 therethrough and into scalp 30.

Referring now to FIGS. 2 and 3, one preferred pattern for cannula 20 in stereotaxic plug 18 includes a cross shape having a central cannula 20A surrounded by four peripheral cannula 20B. Six marker bores 28 are disposed along each of the axes of the crosses formed by cannula 20, with three on each side. As noted in the above-referenced U.S. Patent, the edge of counterbore 26 may contain flattened portions (not shown) for enabling insertion of stereotaxic plug 18 into threaded opening 12.

Marker cannula 34 and radiopaque markers 36 in marker button 32 (FIG. 3) are disposed in precisely the same relative positions as are cannula 20 and marker bores 28 in stereotaxic plug 18, respectively. In addition, four suture holes 38 are disposed about the circumference of marker button 32.

In use, stereotaxic plug 18 is installed in the skull in the manner disclosed in my above-referenced U.S. Patent. The location of stereotaxic plug 18 and of cannula 20 with respect to an underlying tumor is determined from an image of the skull and brain, including an image of marker bores 28. Then scalp 30 (FIG. 1) is closed over threaded opening 12 and stereotaxic plug 18 to prevent infection. Marker button 32 is positioned over scalp 30 and radiopaque markers 36 are aligned with marker bores 28. This positioning is enabled by medical imaging showing all of the radiopaque markers in the same view. A suture 40 is installed in one suture hole 38 to provide displacement stability of marker button 32, but to permit it to be rotated about suture 40 into a final alignment. The remaining three sutures 40 are then installed. Thereupon, there is created an external image of the cannula 20 in stereotaxic plug 18.

A catheter (not shown) such as, for example, the multi-lumen catheter disclosed in my referenced patent application, a hypodermic syringe (not shown), or other device may be inserted through scalp 30, guided by a selected one of marker cannula 34, through its aligned cannula 20 into brain tissue 22 at a precisely determined angle. The size of the wound produced in scalp 30 by the insertion of a catheter is on the order of that produced by insertion of a medical syringe. Thus, normal hygiene employed to prevent infection attendant to the administration of an injection is sufficient.

In the case of my referenced multi-lumen catheter, radiopaque markings at predetermined locations along its length provide a reference from which the physician may determine the depth of penetration of the catheter into brain tissue 22 aided by medical imaging devices. This provide the third dimension in locating the catheter.

Besides its value in guiding the insertion of medical devices into stereotaxic plug 18, the presence of marker button 32 also increases the length over which the inserted medical device is supported. This further improves the accuracy within which the position on scalp 30 and the angle of insertion of a medical device can be controlled.

Figure 5:
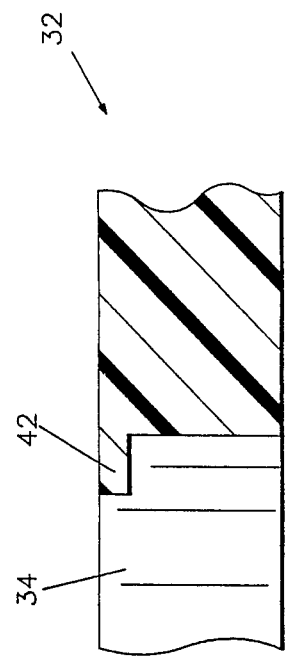
FIG. 5 is a cross section taken along V—V in FIG. 4.

Referring now to FIG. 4, a close-up view of marker cannula 34 reveals the presence of three jaws 42, spaced 180 degrees apart. Referring now also to FIG. 5, in one embodiment of the invention jaws 42 are disposed in marker cannula 34 adjacent an upper surface of marker button 32. This provides additional stability for an inserted medical device.

Stereotaxic plug 18 may also be provided with jaws 42 (not shown) preferably disposed near an inner end of threaded body 16. When jaws 42 are included in both stereotaxic plug 18 and marker button 32, guidance of an inserted medical device takes place at two widely spaced longitudinal positions, whereby accuracy is enhanced. In addition to improved guidance, jaws 42 may provide clamping action on the surface of an inserted device since the opening therebetween can be made slightly undersize, whereby the resilience of the material from which stereotaxic plug 18 and marker button 32 are made may provide a clamping action.

Referring now to FIG. 6, a marker button 32 is shown in use by itself for treatment of a tumor 44 in soft tissue such as, for example, a breast 46. Marker button 32 is positioned in the required location aided by medical imagery showing both tumor 44 and the pattern produced by radiopaque markers 36. It is then fixed in place using sutures 40 through suture holes 38 and into the underlying tissue.

In use, marker button 32 provides an external guide to the insertion of medical devices into tumor 44 without requiring new medical images each time treatment is to be performed. This reduces the exposure of a patient to ionizing radiation and reduces the cost of treatment. The reduction in treatment cost is enhanced by the opportunity to perform follow-on treatment in locations lacking medical imaging devices such as, for example, a hospital room or a physician's office.

It would be clear to one skilled in the art that the material employed in marker bores 28 and radiopaque markers 36 (FIG. 1) vary according to the type of imaging device. For example, an imaging device relying on short-wavelength X-ray or emission tomography requires a material having a large absorptivity at the operating wavelength. One suitable material is gold. Nuclear magnetic resonance imaging (NMRI) relies on the emission of radio waves by spinning atomic nuclii to image soft tissue. In many applications, advantage is taken of the presence in the body of materials having good emitting properties such as, for example, water and lipids. These materials emit signals at radio signals at frequencies related to the type of material and the magnetic field strength of the polarizing magnet. To be visible in an NMRI device, marker bores 28 and radiopaque markers 36 preferably contain a material capable of emitting a radio signal in the same spectrum as the tissue being imaged.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What I claim is:

1. A stereotaxic array locating system for locating a displacement and angle of insertion of a medical instrument, comprising:
   a stereotaxic array plug;
   said stereotaxic array plug including a first plurality of first cannula disposed in a first pattern;
   said stereotaxic array plug further including a second plurality of first markers in a second pattern;
   said second pattern having a predetermined relationship to said first pattern;
   said first markers being of a type visible on a medical imaging device;
   said stereotaxic array plug including means for permitting insertion thereof into an opening in a skull;
   a marker button;
   said marker button including a third plurality of second cannula disposed in a third pattern;
   said marker button further including a fourth plurality of second markers in a fourth pattern;
   said second markers being of a type visible on said medical imaging device;
   said marker button further including means for permitting stable attachment thereof to a scalp;
   said third pattern being identical to said first pattern;
   said second pattern being identical to said fourth pattern; and
   said first markers and said second markers being capable of simultaneous imaging by said medical imaging device, whereby congruence between said first and second markers resulting in congruence between said first and second cannula is attainable.

2. A stereotaxic array locating system according to claim 1 wherein said means for permitting stable attachment includes a plurality of suture holes spaced apart about a circumference of said marker button.

3. A stereotaxic array locating system according to claim 1 wherein each cannula of said first plurality includes a plurality of inward-directed jaws.

4. A stereotaxic array locating system according to claim 3 wherein said jaws are disposed near an inner end of said stereotaxic array plug.

5. A stereotaxic array locating system according to claim 3 wherein each cannula of said third plurality includes a further plurality of inward-directed jaws.

6. A stereotaxic array locating system according to claim 5 wherein said plurality of jaws in said first cannula are disposed near an inner end of said stereotaxic array plug and said further plurality of jaws are disposed near an outer surface of said marker button.

7. A method for installing a stereotaxic locating system comprising:
   installing a stereotaxic array plug in an opening in a skull;
   said stereotaxic array plug being of a type including a first plurality of first cannula disposed in a first pattern and a second plurality of first markers in a second pattern, said second pattern having a predetermined relationship to said first pattern;
   closing a scalp over said stereotaxic array plug;
   suturing a marker button over said scalp;
   said marker button being of a type including a third plurality of second cannula disposed in a third pattern and a fourth plurality of second markers in a fourth pattern, said first and third patterns being identical and said second and fourth patterns being identical;
   said second markers being of a type visible on said medical imaging device; and
   the step of suturing including aligning said second and fourth patterns using said medical imaging device simultaneously imaging said second and fourth patterns, whereby said first and third patterns are congruent.

* * * * *